United States Patent
Roberts

(10) Patent No.: US 6,171,252 B1
(45) Date of Patent: Jan. 9, 2001

(54) PRESSURE SENSOR WITH INCREASED SENSITIVITY FOR USE WITH AN IMPLANTABLE MEDICAL DEVICE

(75) Inventor: Jonathan P. Roberts, Shoreview, MN (US)

(73) Assignee: Medtronic, Inc., Minneapolis, MN (US)

(*) Notice: Under 35 U.S.C. 154(b), the term of this patent shall be extended for 0 days.

(21) Appl. No.: 09/301,886

(22) Filed: Apr. 29, 1999

(51) Int. Cl.[7] .................................................. A61B 5/02
(52) U.S. Cl. ........................... 600/485; 600/488; 324/678; 702/52; 73/724
(58) Field of Search ..................... 600/481, 485, 600/486, 488; 702/52; 324/679; 73/718, 724

(56) References Cited

U.S. PATENT DOCUMENTS

| | | |
|---|---|---|
| 4,016,764 | 4/1977 | Rice . |
| 4,023,562 | 5/1977 | Hynecek et al. . |
| 4,250,452 * | 2/1981 | Gray et al. ............................... 328/1 |
| 4,257,423 | 3/1981 | McDonald et al. . |
| 4,407,296 | 10/1983 | Anderson . |
| 4,432,372 | 2/1984 | Monroe . |
| 4,485,813 | 12/1984 | Anderson et al. . |
| 4,556,063 | 12/1985 | Thompson et al. . |
| 4,750,495 | 6/1988 | Moore et al. . |
| 4,858,615 | 8/1989 | Meinema . |
| 4,967,755 | 11/1990 | Pohndorf . |
| 5,083,467 * | 1/1992 | Tabota ............................... 73/862.04 |
| 5,113,868 | 5/1992 | Wise et al. . |
| 5,127,404 | 7/1992 | Wyborny et al. . |
| 5,257,210 * | 10/1993 | Schneider et al. ..................... 364/553 |
| 5,324,326 | 6/1994 | Lubin . |
| 5,377,524 | 1/1995 | Wise et al. . |
| 5,535,752 | 7/1996 | Halperin et al. . |
| 5,564,434 | 10/1996 | Halperin et al. . |
| 5,629,629 * | 5/1997 | Tielert et al. ........................ 324/679 |

FOREIGN PATENT DOCUMENTS

WO 94/13200   6/1994   (WO) ............................... A61B/5/03

* cited by examiner

Primary Examiner—Cary O'Connor
Assistant Examiner—Navin Natnithithadha
(74) Attorney, Agent, or Firm—Michael B. Atlass; Harold R. Patton

(57) ABSTRACT

An apparatus and method for obtaining pressure data using a body implantable pressure sensor includes a measurement capacitor which is responsive to pressure changes of a body fluid. Non-constant, multiple current source charging of the measurement capacitor provides for a significant increase in sensitivity to conditions of pressure of a body fluid. Pressure data is obtained by charging the measurement capacitor at a first charge rate during a first charge period of an integration cycle and, during a second charge period of the integration cycle, charging the measurement capacitor at a second charge rate. The first charge rate is preferably greater than the second charge rate. The duration of the first and second charge periods may be varied. A signal indicative of a pressure change of a body fluid imparted to the measurement capacitor is produced by the pressure sensor. The signal may be a signal indicative of a change in a time of integration. The signal, indicative of a time of integration, has a sensitivity to pressure changes which is greater than a mechanical capacitive sensitivity of the measurement capacitor to such pressure changes. The signal may alternatively be a signal indicative of a change in capacitance of the measurement capacitor, such as a voltage signal, or a signal having a duty cycle indicative of the pressure change. The pressure sensor may be implemented in a pacemaker, a pacemaker/cardioverter/defibrillator (PCD) or a hemodynamic monitor.

34 Claims, 7 Drawing Sheets

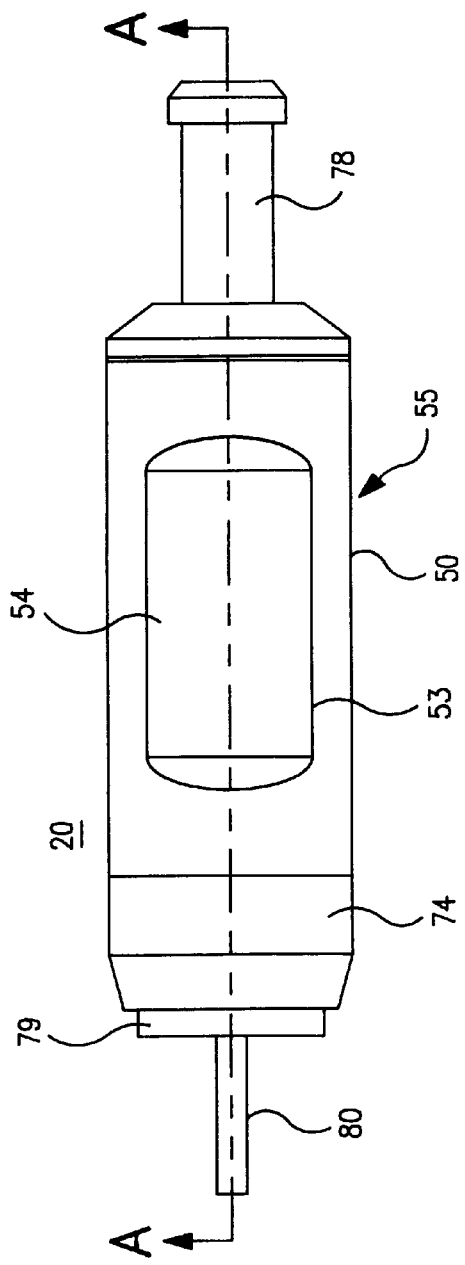
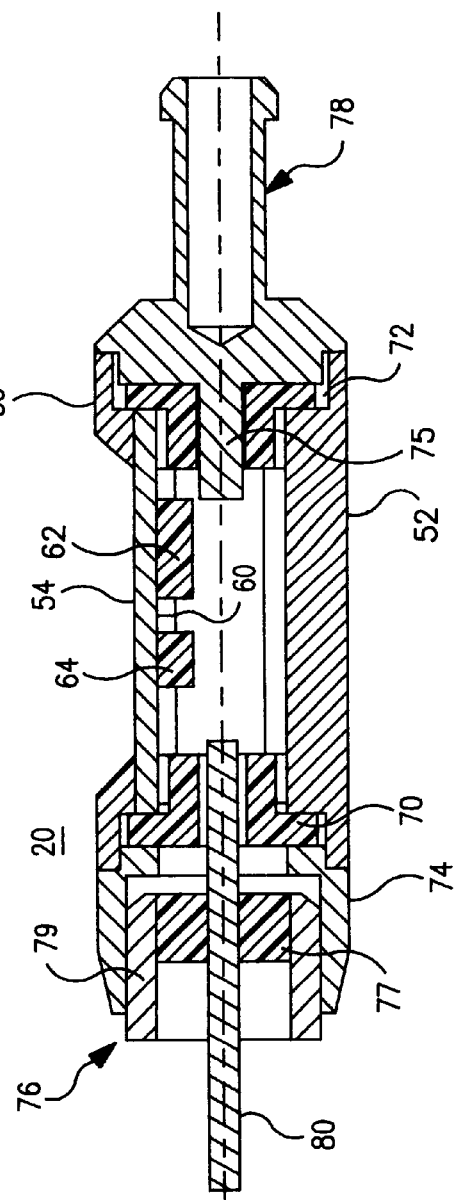
FIG. 2
FIG. 3

PRESSURE SENSOR WITH INCREASED SENSITIVITY FOR USE WITH AN IMPLANTABLE MEDICAL DEVICE

FIELD OF THE INVENTION

The present invention relates generally to pressure sensors adapted for use with an implantable medical device. More particularly, the present invention pertains to a pressure sensor with increased sensitivity that responds to conditions of blood pressure and provides pressure related signals to an implanted hemodynamic monitor and/or cardiac pacemaker or pacemaker/cardioverter/defibrillator. It also can be employed in any implantable medical device which uses a capacitive pickoff sensor.

BACKGROUND OF THE INVENTION

Various implantable medical devices have been developed that receive information from one or more physiologic sensors or transducers. One such physiologic transducer is a pressure sensor that transduces blood pressure into corresponding electrical signals. The electrical signals produced by the pressure sensor are acquired by an implantable medical device via a lead coupled therebetween.

The sensitivity of a body implantable pressure sensor is an important design characteristic. The sensitivity characteristics of an implantable pressure sensor have a direct impact on the signal-to-noise ratio of the pressure sensor signal transmitted to the implantable medical device via the lead coupled therebetween. Increasing the strength of the signal produced by the implantable pressure sensor would therefore appear desirable, as such an increase would result in improved signal-to-noise characteristics and increased integrity of pressure data transmission.

Efforts have been underway for many years to develop implantable pressure transducers and sensors for temporary or chronic use in a body organ or vessel. Many different designs and operating systems have been proposed and placed into temporary or chronic use with patients. Indwelling pressure sensors for temporary use of a few days or weeks are available, and many designs of chronically or permanently implantable pressure sensors have been placed in clinical use.

Many indwelling pressure sensors employ a piezoelectric element or a piezoresistive element as a pressure transducer. Piezoelectric crystals or piezoresistive pressure transducers mounted at or near the distal tips of pacing leads, for pacing applications, or catheters, for monitoring applications, are described in U.S. Pat. Nos. 4,023,562; 4,407,296; 4,432,372; 4,485,813; 4,858,615; 4,967,755; and 5,324,326; and PCT Publication No. WO 94/13200, for example. The desirable characteristics and applications for patient use of such leads or catheter bearing, indwelling pressure sensors are described in these and other patents and the literature in the field.

Other semiconductor sensors employ complimentary metal oxide semiconductor (CMOS) integrated circuit (IC) technology in the fabrication of pressure responsive silicon diaphragm bearing capacitive plates that are spaced from stationary plates. A change in capacitance due to pressure waves acting upon the diaphragm is measured, typically through use of a bridge circuit, as disclosed, for example, in the article "A Design of Capacitive Pressure Transducer" by Ko et al., in IEEE Proc. Symp. Biosensors, 1984, p.32. Fabrication for long term implantation and stability is, however, complicated.

In addition, differential capacitive plate, fluid filled pressure transducers employing thin metal or ceramic diaphragms have also been proposed for large scale industrial process control applications as disclosed, for example, in the article "A ceramic differential-pressure transducer" by Graeger et al., Philips Tech. Rev., 43:4:8693, Feb. 1987. The large scale of such pressure transducers does not lend itself to miniaturization for chronic implantation.

Improved capacitive pressure sensor implementations are disclosed in U.S. Pat. Nos. 5,564,434 and 5,535,752 to Halperin, both of which are incorporated herein by reference in their respective entireties. The '434 and '752 patents disclose a capacitive pressure and temperature sensing system for providing signals representative of absolute pressure and temperature of a body fluid. A sensor module includes a pickoff capacitor and a reference capacitor. The pickoff capacitor changes in capacitance in response to fluid pressure changes, while the reference capacitor is relatively insensitive to fluid pressure changes.

A constant current source provides for charging and discharging of the pickoff and reference capacitors. A pulse generator generates pickoff and reference timing pulses separating pressure related and temperature related charge time intervals of the pickoff and reference capacitors which vary as a function of the charge current and capacitance changes of the pickoff capacitor. Although the capacitive pressure sensing systems disclosed in the '434 and '752 patents provide for accurate sensing of body fluid pressure, a pressure sensing approach having increased sensitivity may be desirable in certain applications.

Despite the considerable effort that has been expended in designing such pressure sensors, a need continues to exist for a body implantable pressure sensor for accurately sensing the pressure of a body fluid which is not subject to mechanical limitations of conventional capacitive transducers. There continues to exist a need for a pressure sensing system that provides for improved sensitivity beyond that provided by a conventional mechanical pressure-to-capacitance transducer. The present invention fulfills these and other needs.

SUMMARY OF THE INVENTION

The present invention is directed to an apparatus and method for obtaining pressure data using a body implantable pressure sensor. The pressure sensor may be provided in a lead for use with a body implantable medical device. Alternatively, the pressure sensor may be incorporated into an implantable device locatable anywhere within the body, such as the heart, brain or other organ or vessel, which transduces pressure of a body fluid to corresponding electrical signals. The pressure sensor may communicate pressure data to a receiving device provided internal to, or externally of, the body, such as an implantable pace generator or an external programmer system, respectively.

The pressure sensor includes a measurement capacitor which is responsive to pressure changes of a body fluid. A technique employing non-constant, multiple current source charging of the measurement capacitor provides for a significant increase in sensitivity to changes in body fluid pressure. Obtaining pressure data using a pressure sensor in accordance with the principles of the present invention involves charging a measurement capacitor at a first charge rate during a first charge period of an integration cycle. During a second charge period of the integration cycle, the measurement capacitor is charged at a second charge rate. The first charge rate is preferably greater than the second charge rate. The duration of the first charge period or of the second charge period may be varied.

Using the measurement capacitor, a signal indicative of a pressure change of a body fluid imparted to the measurement capacitor is produced. The signal indicative of a body fluid pressure change may be a signal indicative of a change in a time of integration. The signal, indicative of a time of integration, has a sensitivity to pressure changes which is greater than the mechanical capacitive sensitivity of the measurement capacitor to such pressure changes.

More particularly, a relative change in a time of integration, which may be characterized by $\Delta t/T$, in response to a body fluid pressure change is greater than a relative change in the capacitance of the measurement capacitor, which may be characterized by $\Delta C/C$, in response to the pressure change, where $\Delta t$ represents the change in integration time during the integration cycle of duration T, and $\Delta C$ represents the change in capacitance, C, of the measurement capacitor. The signal indicative of a body fluid pressure change may alternatively be a signal indicative of a change in capacitance of the measurement capacitor, such as a voltage signal or a signal having a duty cycle indicative of the pressure change.

A pressure sensor for obtaining pressure data according to the present invention includes a switch which is coupled to the measurement capacitor. Also coupled to the switch is a first current source and a second current source. A timing circuit controls the switch to selectively couple the first and second current sources to the measurement capacitor in response to a switch signal produced by the timing circuit. The timing circuit may include a reference capacitor that is substantially insensitive to changes in pressure, and which produces the switch signal. The switch signal may alternatively be produced by another timing device, such as an oscillator or other type of timer.

The switch couples the first current source to the measurement capacitor for charging the measurement capacitor at a first charge rate during a first charge period of an integration cycle. In response to a switch signal produce by the timing circuit, the switch couples the second current source to the measurement capacitor for charging the measurement capacitor at a second charge rate during a second charge period of the integration cycle. The pressure sensor produces a signal indicative of a pressure change of the body fluid imparted to the measurement capacitor. The timing circuit may vary the duration of the first charge period or a duration of the second charge period.

The pressure sensor and pressure sensing methodology of the present invention may be implemented in a wide variety of body implantable medical devices which utilize a lead that incorporates a capacitive pressure sensor. Such implantable medical devices include, for example, a pacemaker, a pacemaker/cardioverter/defibrillator (PCD) or a hemodynamic monitor.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 2 is a top subassembly drawing of a pressure sensing module incorporated into the distal end of a pressure sensing lead;

FIG. 3 is a side cross-section view of the internal components of the pressure sensing module taken along line A—A of FIG. 2;

Figure 1:
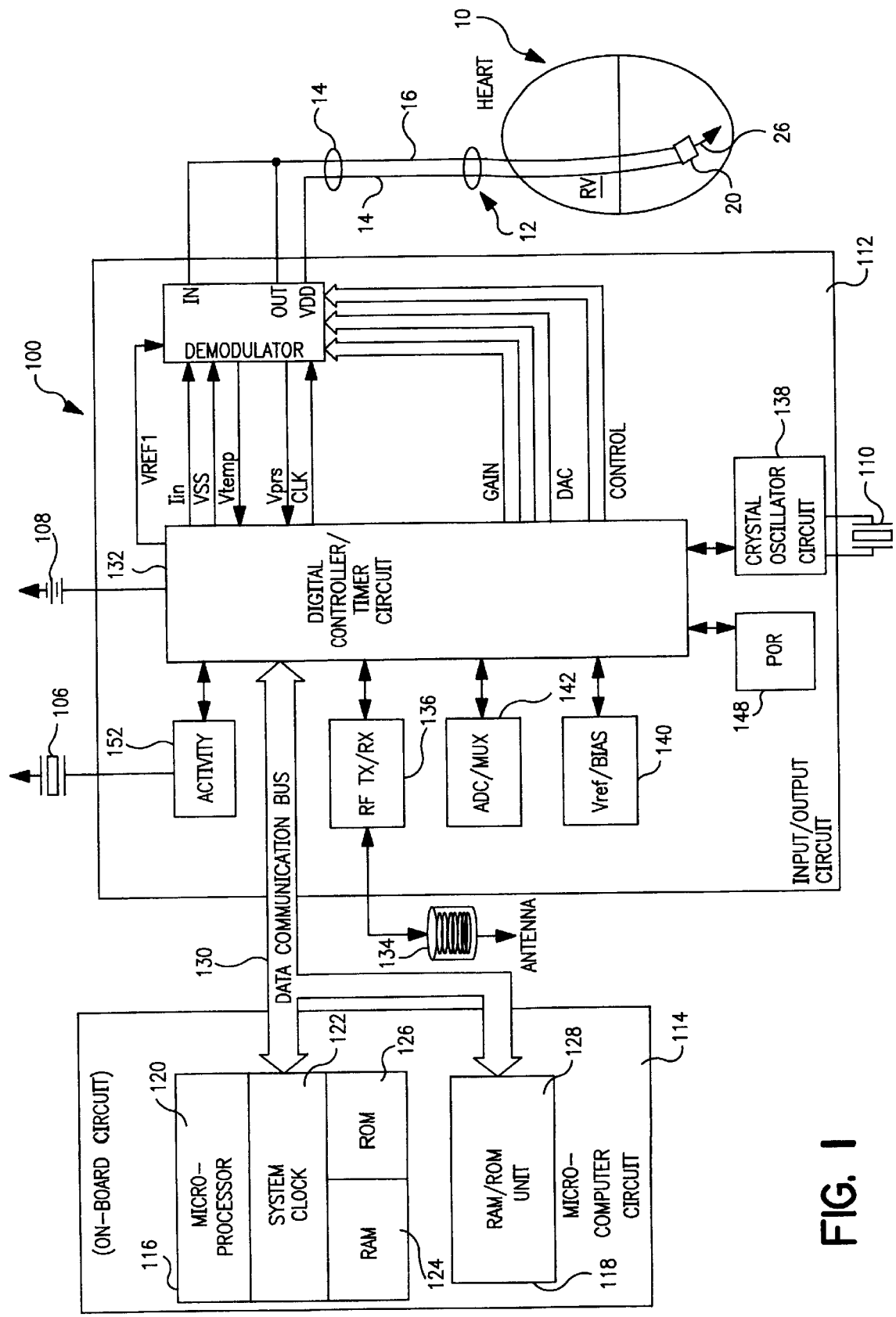
FIG. 1 is block level diagram of an implantable, programmable blood pressure monitor and lead system with which a pressure sensing methodology of the present invention may be practiced.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In accordance with a preferred embodiment of the present invention, and with reference to FIG. 1, the inventive apparatus and methods of the present invention are incorporated into a capacitive pressure sensing lead 12 which is designed to chronically transduce blood pressure from the right ventricle of the heart. The lead 12 is primarily employed with an implantable, battery powered monitor 100 which employs a microprocessor based demodulation, data storage, and telemetry system for sampling and storing blood pressure data at programmed intervals and telemetering out the accumulated data to an external programmer/transceiver on receipt of a programmed-in command, in the manner of current, conventional multi-programmable pacemaker technology. The lead 12 is intended to be implanted transvenously into the right heart chambers in the same manner as a conventional pacing lead, except that the distal end, including the pressure sensor module, may be advanced out of the right ventricle into the pulmonary artery to monitor blood pressure in that location. The monitor is intended to be implanted subcutaneously in the same manner that pacemakers are implanted.

FIG. 1 is a simplified block diagram of the patient's heart 10 in relation to the pressure sensing lead 12 and monitor 100. The lead 12 has first and second lead conductors 14 and 16 extending from a proximal connector end 18 to the pressure sensor module 20 disposed near the distal tine assembly 26. The pressure sensor module 20 includes a variable pickoff capacitor, a fixed reference capacitor, and a signal modulating circuit as will be described hereinbelow in greater detail with reference to FIGS. 2–6. The proximal connector assembly is formed as a conventional bipolar, in-line pacing lead connector and is coupled to the monitor connector (not shown) which is formed as a conventional bipolar in-line pacemaker pulse generator connector block assembly. The tine assembly 26 comprises soft pliant tines adapted to catch in heart tissue to stabilize the lead 12 in a manner well known in the pacing art.

The monitor 100 is divided generally into an input/output circuit 112 coupled to a battery 108, an optional activity sensor 106, a telemetry antenna 134, the lead conductors 14, 16, a crystal 110, and a microcomputer circuit 114. The input/output circuit 112 includes the digital controller/timer circuit 132 and the associated components including the crystal oscillator 138, power-on-reset (POR) circuit 148, $V_{ref}$/BIAS circuit 140, ADC/MUX circuit 142, RF transmitter/receiver circuit 136, optional activity circuit 152, and pressure signal demodulator 150.

Crystal oscillator circuit 138 and crystal 110 provide the basic timing clock for the digital controller/timer circuit 132. The $V_{ref}$/BIAS circuit 140 generates stable voltage reference, $V_{ref}$, and current levels from battery 108 for the circuits within the digital controller/timer circuit 132, and the other identified circuits including microcomputer circuit 114 and demodulator 150. Analog-to-digital converter (ADC) and multiplexor circuit 142 digitizes analog pressure signals, $V_{prs}$, received by digital controller/timer circuit 132 from demodulator 150 for storage by microcomputer circuit 114.

Data signals transmitted out through RF transmitter/receiver circuit 136 during telemetry operations are multiplexed by ADC/MUX circuit 142. Voltage reference and bias circuit 140, ADC/MUX circuit 142, POR circuit 148, crystal oscillator circuit 138, and optional activity circuit 152 may correspond to any of those presently used in current marketed, implantable cardiac pacemakers.

The digital controller/timer circuit 132 includes a set of timers and associated logic circuits connected with the microcomputer circuit 114 through the data communications bus 130. Microcomputer circuit 114 contains an on-board chip including microprocessor 120, associated system clock 122, and on-board RAM and ROM chips 124, 126, respectively. In addition, microcomputer circuit 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on the bus 130, and the receipt of programming signals. A real time clock and calendar function may also be included to correlate stored data to time and date.

Microcomputer circuit 114 controls the operating functions of digital controller/timer 132, specifying which timing intervals are employed, and controlling the duration of the various timing intervals, via the bus 130. The specific current operating modes and interval values are programmable. The programmed-in parameter values and operating modes are received through the antenna 134, demodulated in the RF transmitter/receiver circuit 136 and stored in RAM 124.

Data transmission to and from the external programmer (not shown) is accomplished by means of the telemetry antenna 134 and the associated RF transmitter and receiver 136, which serves both to demodulate received downlink telemetry and to transmit uplink telemetry. For example, circuitry for demodulating and decoding downlink telemetry may correspond to that disclosed in U.S. Pat. Nos. 4,556,063 to Thompson et al. and 4,257,423 to McDonald et al., while uplink telemetry functions may be provided according to U.S. Pat. No. 5,127,404 to Wyborny et al., all of which are hereby incorporated by reference in their respective entireties. Uplink telemetry capabilities will typically include the ability to transmit stored digital information, as well as real time blood pressure signals.

A number of power, timing, and control signals are applied by the digital controller/timer circuit 132 to the demodulator 150 to initiate and power the operation of the pressure sensor module 20 and selectively read out pressure signals, $V_{prs}$. An active lead conductor 16 is attached through the connector block terminals to input and output terminals of demodulator 150 which supplies a voltage, $V_{REG}$, at the output terminal. A passive lead conductor 14 is coupled through to the $V_{DD}$ supply terminal of the demodulator 150. The voltage signal, $V_{prs}$, developed from intervals between current pulses received at the input terminal are provided by demodulator 150 to the digital controller/timer circuit 132. The voltage signal, $V_{prs}$, is converted to binary data in an ADC/MUX circuit 142 and stored in RAM/ROM unit 128 in a manner well known in the art.

As depicted in FIG. 1, the monitor 100 periodically stores digitized data related to blood pressure at a nominal sampling frequency which may be related to patient activity level, both optionally correlated to time and date and patient initiated event markers. The monitor 100 may also optionally include a further lead connector for connection with an additional lead for implantation in the right heart having an exposed unipolar distal electrode from which an electrogram (EGM) may be derived. The additional lead may also have an oxygen sensor module and/or a temperature module in the distal segment of the lead. One exemplary lead is shown in commonly assigned U.S. Pat. No. 4,750,495 to Moore and Brumwell, incorporated herein by reference in its entirety. An appropriate modification to the monitor 100 would include an EGM sense amplifier (using the monitor case as an indifferent electrode) and an oxygen sensor demodulator, and is also described in the above-incorporated patent to Moore and Brumwell.

Other leads which may be provided with capacitive pressure sensors for operation in accordance with the principles of the present invention include those described in the following U.S. Pat. Nos. 5,564,434 and 5,535,752 to Halperin; 5,113,868 and 5,377,524 both to Wise et al.; and 4,016,764 to Rice, all of which are hereby incorporated by reference in their respective entireties.

The sampled and stored blood pressure data are preferably absolute pressure values and do not account for changes in barometric pressure affecting the ambient pressure load on the pressure sensor module 20. Physicians typically measure blood pressure in relation to atmospheric pressure. Thus, it may be necessary to separately record atmospheric pressure data with separate measuring and recording equipment. At present, a separate, portable pressure recording unit (not shown) worn externally by the patient to record atmospheric pressure is contemplated to be used with the system of the present invention. The atmospheric pressure and a time and date tag are preferably recorded in the external unit at periodic, e.g. one minute, intervals. The atmospheric pressure data is intended to be read out from the external unit when the absolute pressure and optional other data stored in RAM/ROM unit 128 is telemetered out and the data correlated by time and date and employed by the physician to derive diagnoses of the patient's condition.

As will be described in greater detail with reference to FIGS. 2 and 3, the pressure sensor capsule or module 20 is constructed with a titanium outer housing having an integral, pressure deformable, planar sensing membrane or diaphragm formed in it as one plate of a variable or pickoff capacitor, $C_P$. The other plate of the pickoff capacitor, $C_P$, is fixed to one side of a hybrid circuit substrate hermetically sealed within the outer housing. The capacitance of pickoff capacitor, $C_P$, varies as the diaphragm is deformed by pressure waves associated with heart beats in the patient's heart 10 or elsewhere in the vascular system. A reference capacitor, $C_R$, is also formed with fixed spacing between planar capacitor plates formed on the same side of the hybrid circuit substrate and on the outer housing to provide a reference capacitance value. The pressure sensor circuitry within the module 20 employs the voltages $V_{DD}$ and $V_{REG}$ supplied by the demodulator 150 to alternately charge and discharge the capacitor pair with charge and discharge currents to provide for the measurement of instantaneous absolute blood pressure change.

Concerning the construction of the pressure sensing capsule or module 20, reference is made to the enlarged top and side cross-sectional views of FIGS. 2 and 3. The pressure sensing module 20 is formed with first and second titanium outer housing half members 50 and 52 which, when joined together as assembled titanium housing 55, surround a ceramic hybrid circuit substrate 60 supporting the sensing and reference capacitors and pressure signal modulating circuit. The pressure signal processing circuit, which is described in detail hereinbelow with reference to FIG. 4, includes a resistor 62 and IC chip 64 mounted to one surface of the substrate 60 and attached to electrical terminal pads and board feed throughs to the other surface thereof. After the mechanical and electrical components of the pressure sensing module 20 are assembled together, the titanium housing half members 50 and 52 and the nose element and adapter ring 74 are laser welded together as hermetically sealed, assembled titanium housing 55. Then, the module 20 is attached to the components of the lead 12 to provide the electrical and mechanical connections with the outer and inner, passive and active, coiled wire lead conductors 14 and 16.

The thin titanium diaphragm 54 is machined into the titanium outer housing half member 50. The flat inner surface of diaphragm 54 and a peripheral continuation of that surface form plates of a pair of planar capacitors, the other plates of which are deposited onto the adjacent surface 61 of the ceramic hybrid substrate 60. An external pressure change results in displacement of the diaphragm 54 and subsequent change in capacitance between the diaphragm 54 and one of the deposited substrate plates. This change in capacitance of the pickoff capacitor, $C_P$, with change in pressure is approximately linear over the pressure range of interest, and is used as a measure of the pressure outside the sensor module 20. The external pressure change has little effect on the second, reference capacitor, $C_R$. To electrically isolate diaphragm 54 from the patient's body, materials must be used that do not significantly absorb body fluids and swell, which in turn causes undesirable diaphragm deflection and changes in the capacitance of the pickoff capacitor, $C_P$.

Figure 4:
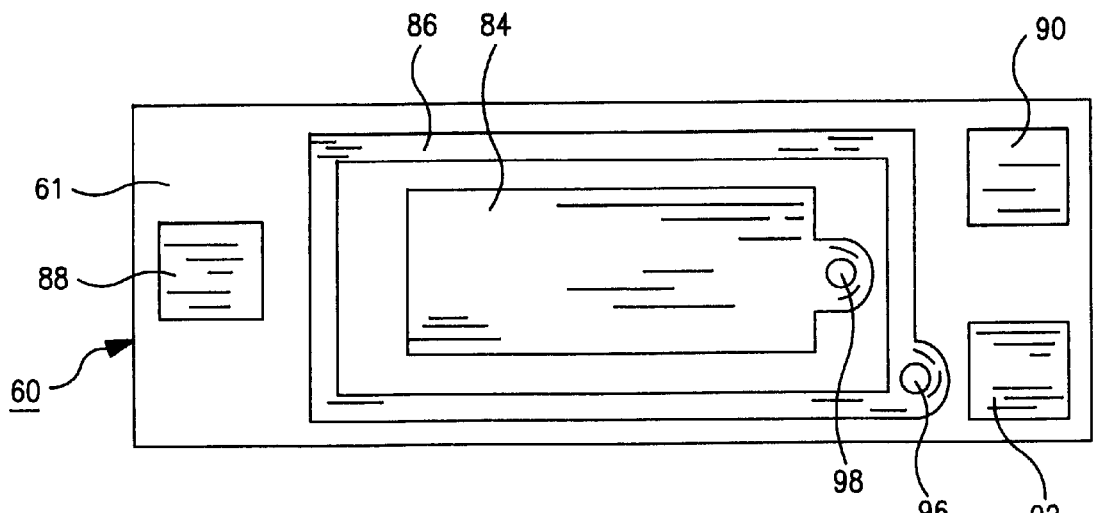
FIG. 4 is a bottom view of the components of the pressure sensing module incorporated on an IC hybrid circuit substrate.

Turning to FIG. 4, the ceramic sensor hybrid circuit substrate 60 consists of a 90% alumina board, on the back side 61 of which are deposited an inner, rectangular capacitor plate 84 coupled to a plated substrate feedthrough 98, an outer, ring shaped capacitor plate 86 coupled to a plated substrate feedthrough 96, and three plated standoffs 88, 90, 92. The inner capacitor plate 84 is dimensioned to generally conform to the shape of the diaphragm 54 and fall within the perimeter 53. The perimeter or ring-shaped capacitor plate 86 is dimensioned to fall outside or just inside or to straddle the perimeter 53. The inner surface 51 of half member 50 provides a reference surface for locating the capacitor plates 84 and 86 relative to the diaphragm 54.

When assembled, the plates 84 and 86 are spaced from the inner surface 51 of the housing half member 50 by the difference in thicknesses of the standoffs 88–92 and the plates 84 and 86 to form the pickoff capacitor, $C_P$, and reference capacitor, $C_R$. The pressure sensing pickoff capacitor, $C_P$, employing central capacitor plate 84 varies in capacitance with pressure induced displacement of the diaphragm 54 and a silicone adhesive layer applied thereto. The reference capacitor, $C_R$, employing the perimeter reference capacitor plate 86 located in the region where diaphragm 54 deflection is negligible within the operating pressure range, varies in capacitance with common mode changes in sensor voltages, thermal expansion effects, and changes in the hermetically sealed capacitor dielectric constant. The two capacitor plates 84 and 86 are electrically connected to the front side of the substrate 60, on which the sensor electronic circuit included in the IC chip 64 and the resistor 62 are mounted. The common capacitor plate surface 51 is coupled to VDD.

In general, changes in blood pressure cause an increase or decrease in plate spacing of the pickoff capacitor, $C_P$, which causes a decrease or increase, respectively, in the capacitance and subsequent decrease or increase, respectively, in the time to charge the pickoff capacitor, $C_P$, to a set voltage level, $V_{REF}$. Since no significant gap change between common plate surface 51 and the perimeter capacitor plate 86 due to pressure change occurs at the reference capacitor, $C_R$, there is no appreciable pressure induced reference capacitance changes in the reference capacitor, $C_R$.

In accordance with the principles of the present invention, the pressure sensor electronic circuitry alternately charges and discharges the pickoff and reference capacitors, $C_P$ and $C_R$, using a non-constant, multiple current source charging methodology. A pressure sensing approach of the present invention provides for a significant increase in sensitivity to changes in pressure over prior art approach that utilize a constant current charging approach through employment of multiple charging currents, as will described in greater detail hereinbelow.

For purposes of illustrating several advantages realized through implementing a pressure sensing methodology according to the present invention, the following analyses are provided. References will be made to FIGS. 5 and 6 which respectively illustrate a prior art pressure sensor circuit, which utilizes a single, constant current source charging approach, and a pressure sensor circuit according to a preferred embodiment of the present invention, which utilizes a non-constant, multiple current source charging approach.

A fundamental formula that controls an integrator circuit which includes a capacitor is given as:

$$V = \int_0^T \frac{I}{C} * dt \quad [1]$$

where, V represents the voltage across the capacitor, C represents capacitance, and T represents the total integration time, which typically represents the amount of time to bring the voltage, V, across the capacitor from a first voltage (e.g., 0 V) to a reference voltage (e.g., $V_{ref}$). In the case in which constant currents are used, such as in the prior art pressure sensor circuit depicted in FIG. 5, Equation [1] simplifies to:

$$\Delta V = \frac{(I * \Delta T)}{C} \quad [2]$$

which may be re-written as:

$$\Delta T = \frac{(V * C)}{I} \quad [3]$$

The duty cycle, DC, associated with the integrator circuit may thus be characterized by:

$$DC = \frac{T_{high}}{(T_{high} + T_{low})} \quad [4]$$

where, $T_{high}$ represents the total time of charging the capacitor from a first voltage (e.g., 0 V) to a reference voltage (e.g., $V_{ref}$), and $T_{low}$ represents the total time of charging the capacitor from the reference voltage to the first voltage (i.e., discharging).

Figure 5:
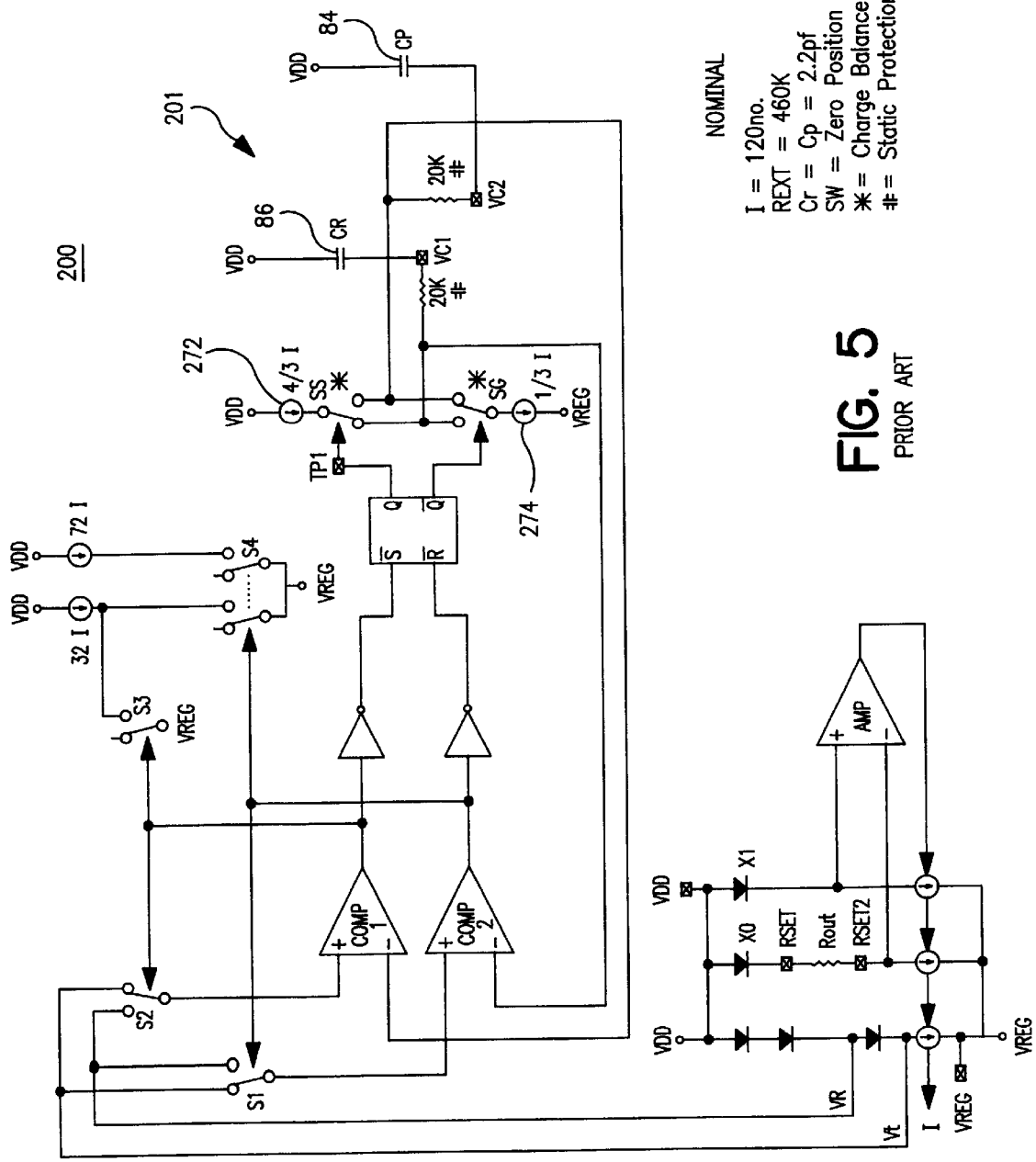
FIG. 5 is a schematic diagram of a pressure sensor circuit which utilizes a single, constant current source charging approach in accordance with a prior art technique.

In the case in which all currents are constant, such as in the prior art circuit of FIG. 5, the equation for integration time may be simplified to:

$$T = \frac{(V * C)}{I} \quad [5]$$

The base frequency for the prior art pressure sensor circuit of FIG. 5 may be given as:

$$\frac{1}{T_{high} + T_{low}} = \frac{I}{V_{ref} * (C_{po} + C_{ref})} \quad [6]$$

where, $C_{po}$ represents pressure sensitive capacitance (i.e., capacitance of the pickoff capacitor), $C_{ref}$ represents non-pressure sensitive capacitance (i.e., capacitance of the reference capacitor), $V_{ref}$ represents a reference voltage to which the capacitor is charged, and I represents the charging current, such as a charging current of ⅓ I provided by constant current source 274 in FIG. 5.

The prior art pressure sensor circuit of FIG. 5 effectively incorporates an oscillator having an ideal duty cycle which is given by:

$$DC = \frac{\frac{V_{ref} * C_{po}}{I}}{\frac{V_{ref} * C_{po}}{I} + \frac{V_{ref} * C_{ref}}{I}} = \frac{C_{po}}{C_{po} + C_{ref}} \quad [7]$$

Using the equations provided above, the ideal sensitivity of the prior art pressure sensor circuit of FIG. 5 with respect to changes in pressure is given as:

$$\frac{\Delta DC}{\Delta P} = \frac{C_{po} + \frac{\Delta C}{\Delta P}}{C_{po} + \frac{\Delta C}{\Delta P} + C_{ref}} - \frac{C_{po}}{C_{po} + C_{ref}} \approx \frac{\frac{\Delta C}{\Delta P}}{4 * C_{po} + 2 * \left(\frac{\Delta C}{\Delta P}\right)} \quad [8]$$

It will be appreciated from Equation [8] above that the sensitivity of the prior art pressure sensor circuit of FIG. 5 with respect to pressure changes is dependent solely upon the mechanical system that makes up the pickoff and reference capacitors, $C_P$ and $C_R$. In actuality, as was verified in computer simulations, the sensitivity of such a circuit is smaller than that suggested in Equation [8] by a factor of approximately 2.

Figure 6:
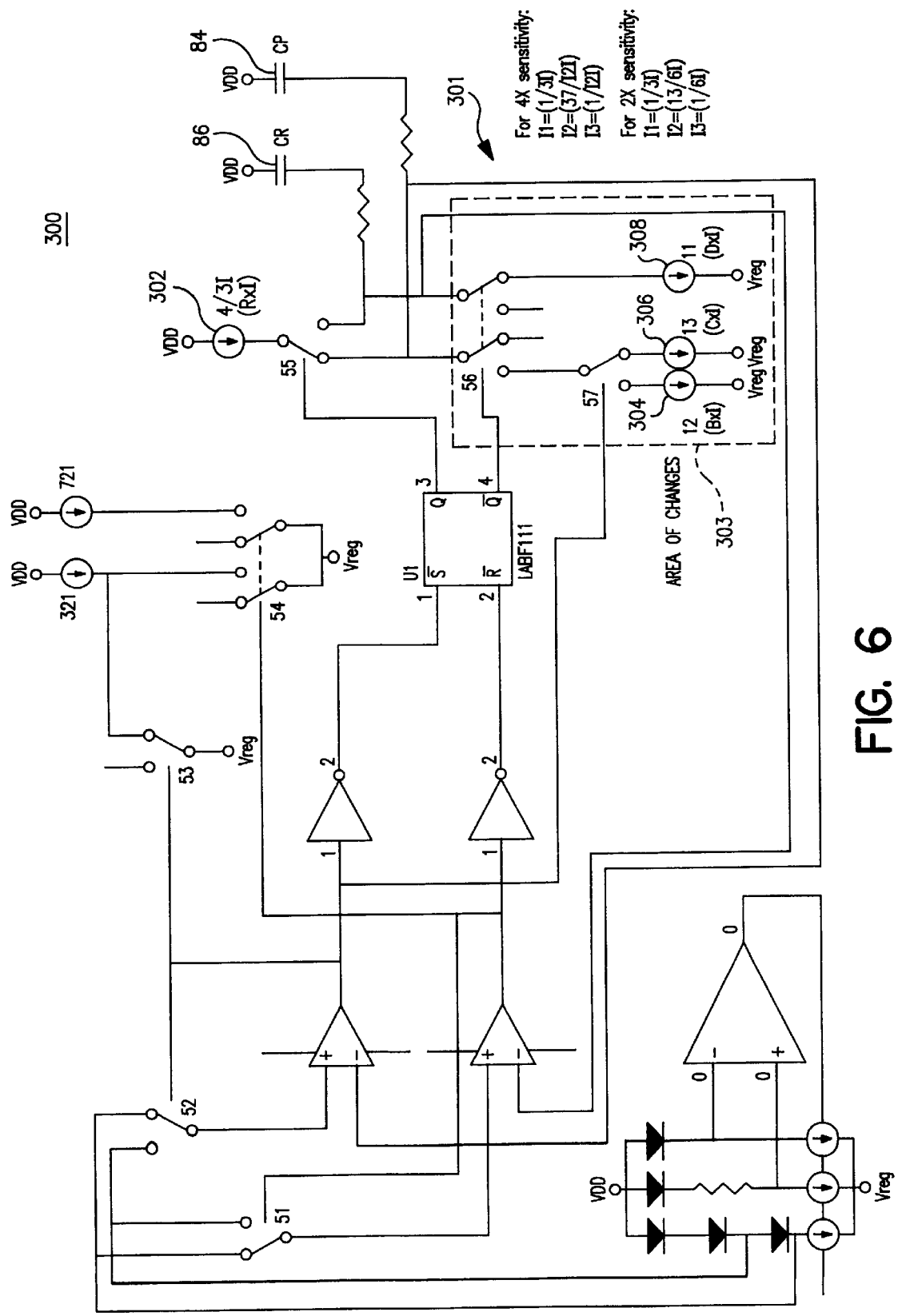
FIG. 6 is a schematic diagram of a pressure sensor circuit which utilizes a non-constant, multiple current source charging approach in accordance with an embodiment of the present invention.

Turning now to FIG. 6, there is illustrated a pressure sensor circuit 300 in accordance with a preferred embodiment of the present invention which advantageously provides for increased sensitivity to pressure changes. In contrast to a prior art pressure sensor circuit which employs a single constant current source, the pressure sensor circuit according to FIG. 6 utilizes a non-constant, multiple current source charging approach for charging the pickoff capacitor, $C_P$. Such an approach provides for a multiple slope integrator circuit which increases the pressure sensing sensitivity of the pressure sensor circuit beyond the mechanical capacitive sensitivity limitations of prior art approaches.

In the embodiment illustrated in FIG. 6, two different source currents are selectively coupled to the pickoff capacitor, $C_P$, within a single integration time period, T. An initial charging current is provided to the pickoff capacitor, $C_P$, during a first charge period of single integration time period, T. The initial charging current is relatively large and quickly places energy on the pickoff capacitor, $C_P$. At an appropriate time, the initial charging current is removed from the pickoff capacitor, $C_P$, and a second charging current is provided to the pickoff capacitor, $C_P$, for the duration of the single integration time period, T. The second charging current is small relative to the initial charging current and slowly places energy on the pickoff capacitor, $C_P$.

The charging current provided to the pickoff capacitor, $C_P$, is switched based on a time which is independent of changes in capacitance. Moreover, this switching time is selectable depending on a number of factors, including dynamic range and noise considerations. By way of example, increasing the time during which the initial charging current (i.e., large charging current) is provided to the pickoff capacitor, $C_P$, provides for an increased dynamic range of operation, but at the cost of increased noise. Increasing the time during which the second charging current (i.e., small charging current) is provided to the pickoff capacitor, $C_P$, provides for a decreased dynamic range, but improved noise characteristics.

With continued reference to FIG. 6, a substantial increase in sensitivity of pressure sensor circuit 300 to pressure changes is realized through employment of non-constant, multiple current source charging of the pickoff capacitor, $C_P$, by the integrator circuit 301. In one embodiment, four regions of linear current are used. The first two regions of linear current are used as sources for charging the pickoff capacitor, $C_P$, in a sequential manner. The first two sources are shown in FIG. 6 as current sources $I_2$ 304 (i.e., B*I) and $I_3$ 306 (i.e., C*I), respectively. The third current source, shown as current source $I_1$ 308 (i.e., D*I), is used for charging the reference capacitor, $C_R$. The fourth current source, shown as current source 302 (i.e., A*I), is used for discharging either the pickoff capacitor, $C_P$, or the reference capacitor, $C_R$.

In general operation, while one of the pickoff capacitor, $C_P$, or the reference capacitor, $C_R$, is charging, the other of the two capacitors is discharging. In accordance with the embodiment shown in FIG. 6, while the reference capacitor, $C_R$, is discharged by one-third, the current provided to the pickoff capacitor, $C_P$, by current source $I_2$ 304 (i.e., B*I) is switched to current source $I_3$ 306 (i.e., C*I). It is noted that the reference capacitor, $C_R$, controls the time at which source current provided to the pickoff capacitor, $C_P$, is switched from current source $I_2$ 304 (i.e., B*I) to current source $I_3$ 306 (i.e., C*I). It is further noted that the switching time is adjustable so as to increase or decrease the time during which each of the respective current sources $I_2$ 304 and $I_3$ 306 provides source current to the pickoff capacitor, $C_P$. Moreover, the switching time may be determined by a timing circuit that employs an oscillator or other timing device as an alternative to using the reference capacitor, $C_R$. As such, switching current sources at a time at which the reference capacitor, $C_R$, is discharged by one-third represents one of many possible switching times and mechanisms, and is provided for purposes of illustration, and not of limitation.

Given the above-description of the general operation of the pressure sensor circuit 300 shown in FIG. 6, the following analysis describes the time, frequency, duty cycle, and sensitivity characteristics of the pressure sensor circuit 300 that advantageously provide for increased sensitivity to pressure changes. Recalling the base frequency of the prior art circuit of FIG. 5 characterized in Equation [4] above, which is expressed in terms of $T_{low}$ and $T_{high}$, the base frequency of the circuit of FIG. 6 is more complex due to multiple current source charging that affects the parameter $T_{high}$, as can be seen in the following equations:

$$T_{low} = \frac{V_{ref} * C_{ref}}{D * I} \quad [9]$$

where, D*I represents the current provided by current source $I_1$ 308, which is used for charging the reference capacitor, $C_R$. The parameter $T_{high}$, may be viewed as comprising two components given by:

$$T_{high} = T(\text{first}) + T(\text{end}) \quad [10]$$

Since T(first) is controlled by the discharge cycle, T(first) may be characterized as:

$$T(\text{first}) = \frac{V_{ref}}{3} * \frac{C_{ref}}{A * I} \quad [11]$$

where, A*I represents the current provided by current source 302, which is used for discharging either the pickoff capacitor, $C_P$, or the reference capacitor, $C_R$. The voltage built up during the first time period, T(first), is given as:

$$V = \frac{B * (C_{ref})(V_{ref})}{3 * A * (C_{po})} \quad [12]$$

where, the term B is associated with current source $I_2$ 304 (i.e., B*I).

The parameter T(end) may be expressed as follows:

$$T(\text{end}) = \left[V_{ref} - \frac{B * (C_{ref})(V_{ref})}{3 * A * (C_{po})}\right] * \frac{C_{po}}{C * I} \quad [13]$$

$$T(\text{end}) = \left[\frac{3 * A * (C_{po}) - B * (C_{ref})}{3 * A}\right] * \frac{V_{ref}}{C * I} \quad [14]$$

$$T(\text{end}) = \left[\left(3 * \frac{A}{C}\right) * (C_{po}) - \left(\frac{B}{C}\right) * (C_{ref})\right] * \frac{(V_{ref})}{(3 * A * I)} \quad [15]$$

Combining the above equations for T(first) and T(end) to arrive at T(high), as given in Equation [10], yields:

$$T_{high} = \frac{(V_{ref})(C_{ref})}{3 * A * I} + \frac{\left[\left(3 * \frac{A}{C}\right) * (C_{po}) - \left(\frac{B}{C}\right) * (C_{ref})\right] * (V_{ref})}{3 * A * I} \quad [16]$$

$$T_{high} = \frac{(3 * A) * (C_{po})(V_{ref}) - (B - C)(C_{ref})(V_{ref})}{3 * A * C * I} \quad [17]$$

The parameter $T_{low}$ may be rewritten as:

$$T_{low} = \frac{C_{ref} * V_{ref}}{D * I} = \frac{\left(3 * A * \frac{C}{D}\right) * C_{ref} * V_{ref}}{3 * A * C * I} \quad [18]$$

The resulting base frequency of the circuit of FIG. 6 may thus be expressed as:

$$\frac{1}{T_{high} + T_{low}} = \frac{\frac{3ACI}{V_{ref}}}{3A(C_{po}) + \left(C - B + \frac{3AC}{D}\right)(C_{ref})} \quad [19]$$

The pressure sensor circuit of FIG. 6 exhibits a duty cycle which is given by:

$$DC = \frac{T_{high}}{(T_{high} + T_{low})} \quad [20]$$

$$DC = \frac{\frac{(3 * A)(C_{po})(V_{ref}) - (B - C)(C_{ref})(V_{ref})}{3 * A * C * I}}{\frac{(3 * A)(C_{po})(V_{ref}) - (B - C)(C_{ref})(V_{ref})}{3 * A * C * I} + \frac{\left(3 * A * \frac{C}{D}\right)(C_{ref}) * (V_{ref})}{3 * A * C * I}} \quad [21]$$

$$DC = \frac{3 * A * C_{po} - (B - C) * C_{ref}}{3 * A * C_{po} + \left(C - B + 3 * A * \frac{C}{D}\right) * C_{ref}} \quad [22]$$

Using the equations presented above, the sensitivity of the pressure sensor circuit of FIG. 6 with respect to changes in pressure is given as:

$$\frac{\Delta DC}{\Delta P} = \frac{3 * A * \left(C_{po} + \frac{\Delta C}{\Delta P}\right) - (B - C) * (C_{po})}{3 * A * \left(C_{po} + \frac{\Delta C}{\Delta P}\right) + \left(C - B + 3 * A * \frac{C}{D}\right) * C_{po}} - \frac{(3 * A - B + C) * C_{po}}{\left(3 * A - B + C + 3 * A * \frac{C}{D}\right) * C_{po}} \quad [23]$$

-continued $$\frac{\Delta DC}{\Delta P} = \frac{(3*A-B+C)*C_{po} + 3*A*\left(\frac{\Delta C}{\Delta P}\right)}{\left(3*A-B+C+3*A*\frac{C}{D}\right)*C_{po} + A*\left(\frac{\Delta C}{\Delta P}\right)} - \qquad [24]$$

$$\frac{(3*A-B+C)}{\left(3*A-B+C+3*A*\frac{C}{D}\right)}$$

$$\frac{\Delta DC}{\Delta P} = \frac{\left(\frac{9AAC}{D}\right)*\left(\frac{\Delta C}{\Delta P}\right)}{\left[\left(3A-B+C+3A*\frac{C}{D}\right)\wedge2\right]*C_{po} +} \qquad [25]$$
$$\left(9AA-3AB+3AC+\frac{9AAC}{D}\right)*\left(\frac{\Delta C}{\Delta P}\right)$$

which may be rewritten in a more generic form of:

$$\frac{\Delta DC}{\Delta P} = \frac{K*\frac{\Delta C}{\Delta P}}{M*C_{po} + (N+K)*\frac{\Delta C}{\Delta P}} \qquad [26]$$

EXAMPLE #1

For purposes of example, it may be desirable to maintain the duty cycle, DC, at 50%, and to transduce blood pressure from the right ventricle of the heart over the range of absolute pressures from 400–900 mm Hg, and within the frequency range of 0–100 Hz. Given these considerations, the following values for the parameters I, D, A, C, and B as used in the above equations are applicable:

I=120 nA
D=⅓
A=⅔
C=1/(3*G)
B=4−11C where, G represents the desired increase in sensitivity. Using these parameter values, the duty cycle calculation of Equations [23–26] simplifies to:

$$\frac{\Delta DC}{\Delta P} = \frac{G*\left(\frac{\Delta C}{\Delta P}\right)}{4*C_{po} + 2*G*\left(\frac{\Delta C}{\Delta P}\right)} \qquad [27]$$

The increase in sensitivity realized through this implementation of the present invention is readily appreciated by comparing the duty cycle expression of Equation [27] associated with the pressure sensor circuit of FIG. 6 with that of Equation [28] below associated with the prior art implementation of FIG. 5:

$$\frac{\frac{\Delta C}{\Delta P}}{4*C_{po} + 2*\left(\frac{\Delta C}{\Delta P}\right)} \qquad [28]$$

It can be seen from a review of Equations [27] and [28] above that the increase in sensitivity resulting from the implementation of FIG. 6 is equivalent in effect to increasing the sensitivity of the sensing membrane or diaphragm which forms one plate of the pickoff capacitor, $C_P$ (e.g., greater AΔ/ΔP with the same total capacitance). It is noted that the sensitivity will be slightly less than the value of G, since there will be an increasing factor of ΔC/ΔP in the denominator of Equation [27] which only becomes a concern with relatively large increases in sensitivity.

EXAMPLE #2

By way of further example, it may be desirable to provide for a 2× increase in sensitivity of the pressure sensor to pressure changes. In such a case, the following values for the parameters I, D, A, C, and B as used in the above equations are applicable:

I=120 nA
D=⅓
A=⅔
C=1/(3*2)=⅙
B=4−11*⅙=13/6

Using these parameter values, the sensitivity is given by:

$$\frac{\left(2*\frac{\Delta C}{\Delta P}\right)}{\left(4*C_{po} + 4*\frac{\Delta C}{\Delta P}\right)} \qquad [29]$$

As was mentioned previously, the examples and equations presented above illustrate time, frequency, duty cycle, and sensitivity characteristics of the pressure sensor circuit 300 in FIG. 6, given the assumption that the current provided to the pickoff capacitor, $C_P$, by current source $I_2$ 304 (i.e., B*I) is switched to current source $I_3$ 306 (i.e., C*I) when the reference capacitor, $C_R$, is discharged by one-third. It was further noted that the switching time is adjustable so as to increase or decrease the time during which each of the respective current sources $I_2$ 304 and $I_3$ 306 provides source current to the pickoff capacitor, $C_P$. The following analysis, in contrast to the specific case exemplified above, further illustrates, in more generic terms, the increase in sensitivity to pressure changes realizable through implementation of a pressure sensor in accordance with the principles of the present invention.

A complete integration time period may be considered to comprise a fast charge time period, $T_1$, and a slow charge time period, $T_2$, both of which are adjustable by appropriate selection of the current source switching time. The fast charge time period, $T_1$, is characterized by the following equation:

$$T1 = \frac{Cref \cdot (Vref - Vrefdb2)}{Idch} \qquad [30]$$

where, $C_{ref}$ represents the non-pressure sensitive capacitance (i.e., capacitance of the reference capacitor, $C_R$), $V_{ref}$ represents the high reference voltage, $V_{refdb2}$ represents the low reference voltage, and $I_{dch}$ represents the discharge current.

The voltage across the pickoff capacitor, $C_P$, after the fast charge time period, $T_1$, is given by:

$$Vpo@T1 = \frac{Ich1 \cdot T1}{Cpo} = \frac{Ich1}{Idch} \cdot \frac{Cref}{Cpo} \cdot (Vref - Vrefdb2) \qquad [31]$$

where, $I_{ch1}$ represents the fast charge current and $C_{po}$ represents the pressure sensitive capacitance (i.e., capacitance of the pickoff capacitor, $C_P$).

The slow charge time period, $T_2$, is characterized by the following equation:

$$T2 = \frac{Cpo \cdot (vref - Vpo@T1)}{Ich2} = \qquad [32]$$
$$\frac{Cpo \cdot Vref}{Ich2} - Cref \cdot \frac{Ich1}{(Ich2 \cdot Idch)} \cdot (Vref - Vrefdb2)$$

where, $I_{ch2}$ represents the slow charge current. The total time of charging the pickoff capacitor, $C_P$, from 0 V to $V_{ref}$ is given by:

$$Tpo = T1 + T2 = \frac{Cref \cdot (Vref - Vrefdb2)}{Idch} + \qquad [33]$$
$$\frac{Cpo \cdot Vref}{Ich2} - Cref \cdot \frac{Ich1}{(Ich2 \cdot Idch)} \cdot (Vref - Vrefdb2)$$

Equation [33] may be rewritten as:

$$Tpo = \left[\frac{Cpo \cdot Vref}{Ich2}\right] - \left[\frac{Cref \cdot (Vref - Vrefdb2)}{\left(\frac{Idch \cdot Ich2}{Ich1 - Ich2}\right)}\right] \qquad [34]$$

where the first and third terms of Equation [33] are combined to produce the second term of Equation [34].

By mirroring the capacitances, the parameter $T_{ref}$ may be derived and characterized by:

$$Tref = \left[\frac{Cref \cdot Vref}{Ich2}\right] - \left[\frac{Cpo \cdot (Vref - Vrefdb2)}{\left(\frac{Idch \cdot Ich2}{Ich1 - Ich2}\right)}\right] \qquad [35]$$

where, $T_{ref}$ represents the total time of charging the reference capacitor, $C_R$, from 0 V to $V_{ref}$.

It can be seen from Equation [34] above that the second term of the equation is a negative term, assuming $I_{ch1} > I_{ch2}$, which reduces the total time, $T_{po}$, of charging the pickoff capacitor, $C_P$, from 0 V to $V_{ref}$. It is noted that if the second term of Equation [34] were zero, the equation would collapse to a characterization of a single constant current integration scenario, such as that described above with respect to the prior art pressure sensor circuit of FIG. 5. It can be further seen from Equation [34] that this reduction in charging time occurs while the derivative $dT_{po}/dp$ remains unchanged, which provides for increased pressure sensor sensitivity as will be discussed further hereinbelow.

The impact of changes in pressure (i.e., changes in $C_{po}$) on $T_{po}$ may be seen in the following equations:

$$\frac{dTpo}{dP} = \frac{d\left(\left[\frac{Cpo \cdot Vref}{Ich2}\right] - \left[\frac{Cref \cdot (Vref - Vrefdb2)}{\left(\frac{Idch \cdot Ich2}{Ich1 - Ich2}\right)}\right]\right)}{dP} \qquad [36]$$

$$\frac{dTref}{dP} = \frac{d\left(\left[\frac{Cref \cdot Vref}{Ich2}\right] - \left[\frac{Cpo \cdot (Vref - Vrefdb2)}{\left(\frac{Idch \cdot Ich2}{Ich1 - Ich2}\right)}\right]\right)}{dP} \qquad [37]$$

Since the pickoff capacitor, $C_P$, is the only pressure sensitive element in pressure sensor circuit 300 of FIG. 6, the derivative formulae of Equations [36] and [37] above may be rewritten below as Equations [38] and [39], respectively, as follows:

$$\frac{dTpo}{dP} = \left[\frac{\frac{dCpo}{dP} \cdot Vref}{Ich2}\right] \qquad [38]$$

$$\frac{dTref}{dP} = -\left[\frac{\frac{dCpo}{dP} \cdot (Vref - Vrefdb2)}{\left(\frac{Idch \cdot Ich2}{Ich1 - Ich2}\right)}\right] \qquad [39]$$

It is important to note that the derivative $dC_{po}/dP$ now shows up in both equations associated with the terms $T_{ref}$ and $T_{po}$, and that the impact of $dC_{po}/dP$ has an opposite sign in the $T_{ref}$ equations relative to the $T_{po}$ equations (see, e.g., Equations [38] and [39] above). It is further important to note that the sensitivity of $T_{po}$ to pressure changes is not impacted by $I_{ch1}$ or $I_{dch}$, and is that same as if there was a constant current integration of $I_{ch2}$. Most of the increase in pressure sensor sensitivity is due to the effective shortening of the total time, $T_{po}$, of charging the pickoff capacitor, $C_P$, which is shorter than if there was constant current integration of $I_{ch2}$, while the derivative $dT/dP$ remains unreduced. The effective increase of the ratio $dT_{po}/T_{po}$ provides for greater pressure sensor sensitivity.

For purposes of further illustration, it is assumed that the pickoff capacitor, $C_P$, is used by the pressure sensor to produce a signal in which a time of integration varies as a function of capacitance changes of the pickoff capacitor, $C_P$. The sensitivity in terms of variations in integration time of this signal in response to pressure changes is greater than the mechanical capacitive sensitivity of the pickoff capacitor, $C_P$, in response to such pressure changes. In other words, a relative change in a time of integration, which may be characterized by $\Delta t/T$, in response to a body fluid pressure change is greater than a relative change in the capacitance of the pickoff capacitor, $C_P$, which may be characterized by $\Delta C/C$, in response to the pressure change, where $\Delta t$ represents the change in integration time during the integration cycle of duration T, and $\Delta C$ represents the change in capacitance, C, of the pickoff capacitor, $C_P$.

In the case in which the duty cycle of the signal produced by the pressure sensor is indicative of pressure change, an additional increase in sensitivity is gained. This additional gain in sensitivity is due to the time parameter $T_{ref}$, which represents the total time of charging the reference capacitor, $C_R$, from 0V to $V_{ref}$. The time parameter $T_{ref}$ has a negative sensitivity to pressure, and since the signal used is a duty cycle (i.e., $T_{po}/(T_{po}+T_{ref})$), the denominator is reduced as a result of an increase in pressure, yielding an additional gain in sensitivity.

The duty cycle, DC, may be calculated using the above equations for $T_{po}$ and $T_{ref}$ as given below:

$$DC = \frac{Tpo}{Tpo + Tref} \qquad [40]$$

$$DC = \frac{\left[\frac{Cpo \cdot Vref}{Ich2}\right] - \left[\frac{Cref \cdot (Vref - Vrefdb2)}{\left(\frac{Idch \cdot Ich2}{Ich1 - Ich2}\right)}\right]}{\left[\frac{(Cpo + Cref) \cdot Vref}{Ich2}\right] - \left[\frac{(Cpo + Cref) \cdot (Vref - Vrefdb2)}{\left(\frac{Idch \cdot Ich2}{Ich1 - Ich2}\right)}\right]} \qquad [41]$$

$$DC = \frac{\left[\frac{Cpo \cdot Vref}{Ich2}\right] - \left[\frac{Cref \cdot (Vref - Vrefdb2)}{\left(\frac{Idch \cdot Ich2}{Ich1 - Ich2}\right)}\right]}{\left[\frac{Cpo \cdot Vref}{Ich2}\right] - \left[\frac{Cref \cdot (Vref - Vrefdb2)}{\left(\frac{Idch \cdot Ich2}{Ich1 - Ich2}\right)}\right] + \left[\frac{Cref \cdot Vref}{Ich2}\right] - \left[\frac{Cpo \cdot (Vref - Vrefdb2)}{\left(\frac{Idch \cdot Ich2}{Ich1 - Ich2}\right)}\right]} \quad [42]$$

Figure 7:
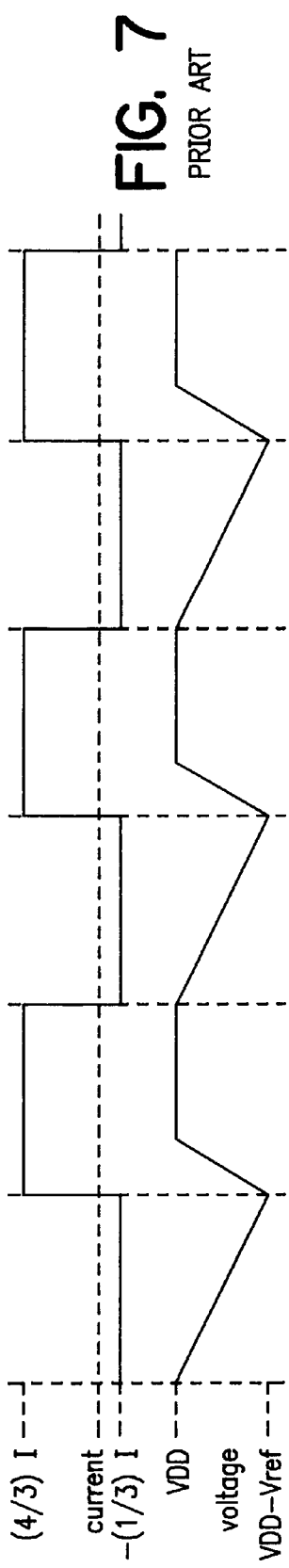
FIG. 7 is a showing of current and voltage waveforms produced by the prior art pressure sensor circuit of FIG. 5.
Figure 8:
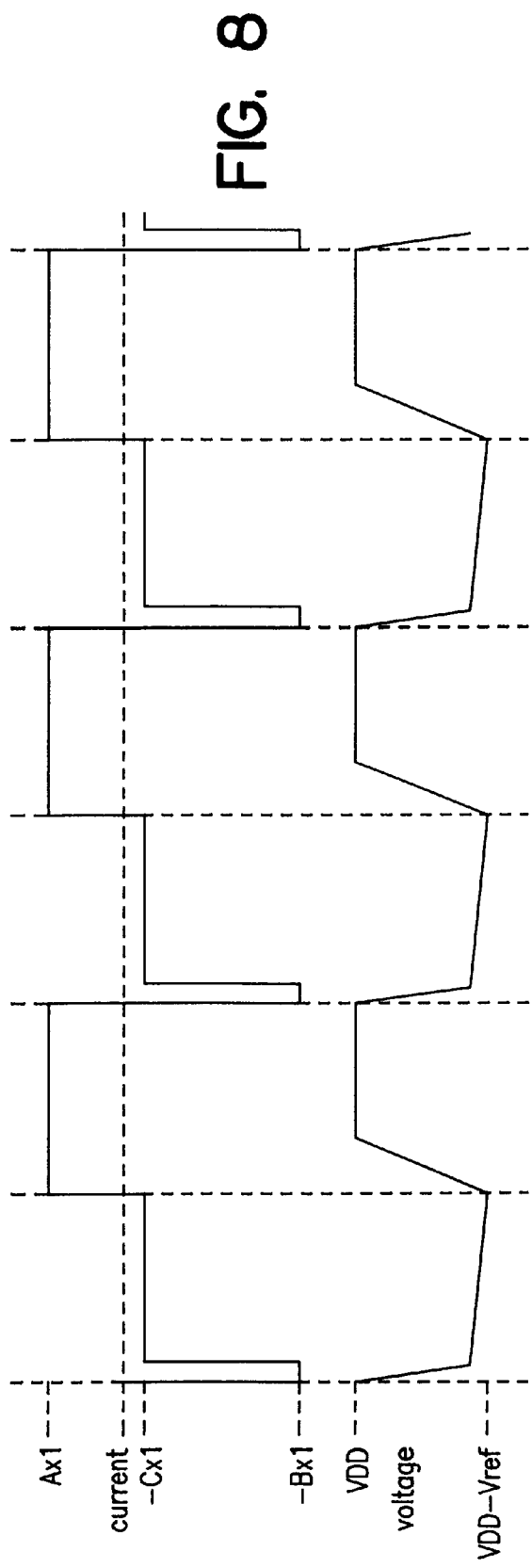
FIG. 8 is a showing of current and voltage waveforms produced by the pressure sensor circuit of FIG. 6 in accordance with the principles of the present invention.

The waveforms shown in FIGS. 7 and 8 illustrate important distinctions between the prior art pressure sensor circuit of FIG. 5 and the pressure sensor circuit of FIG. 6 implemented in accordance with the principles of the present invention. In particular, the waveforms of FIG. 8 clearly demonstrate multiple-slope current and voltage signals through each integration time period, which provides for increased pressure sensing sensitivity as discussed above. FIG. 7, in contrast, depicts single-slope current and voltage signals through each integration time period.

Figure 9:
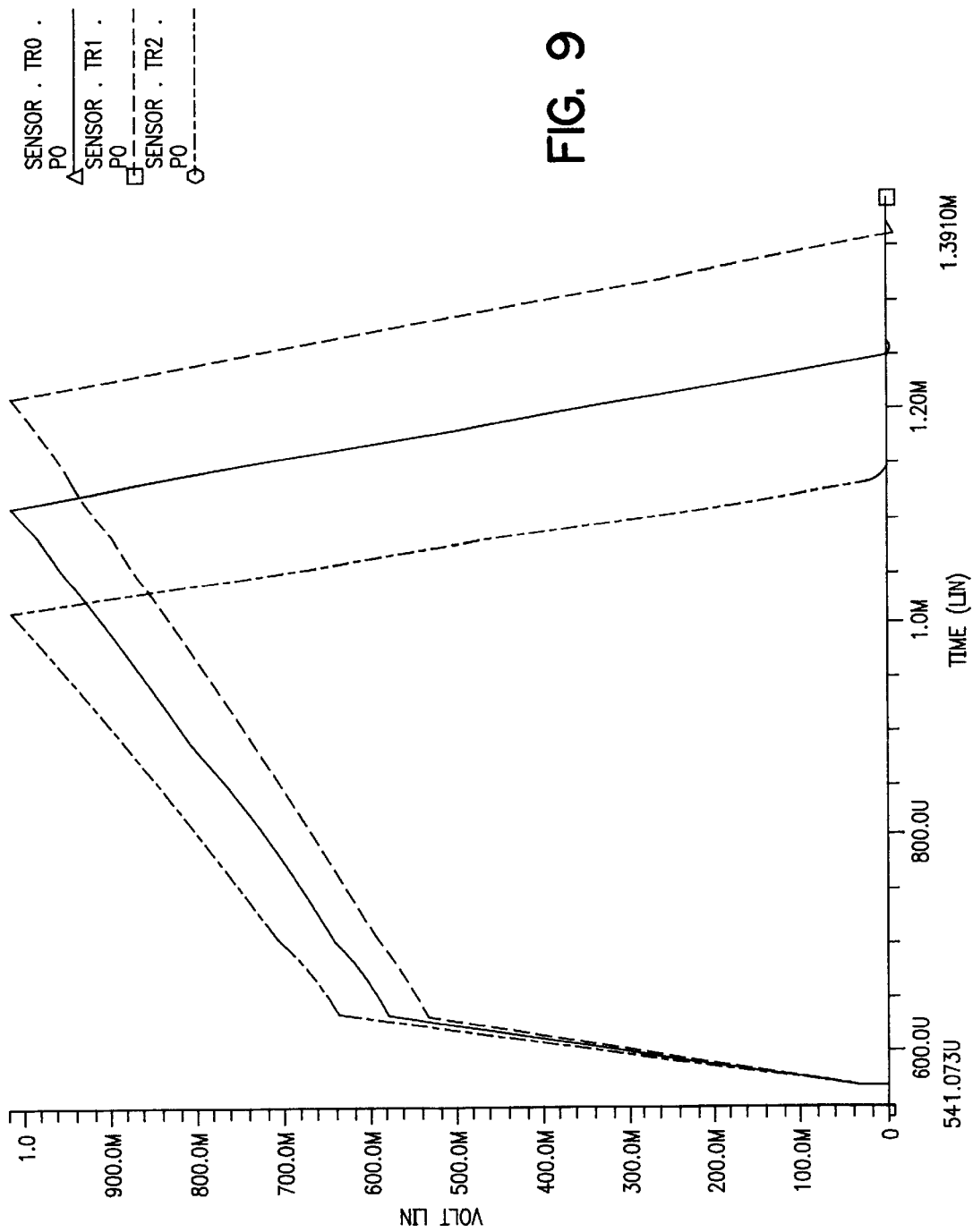
FIG. 9 is a set of dual-slope voltage waveforms produced by the pressure sensor circuit of FIG. 6 in accordance with the principles of the present invention.

FIG. 9 graphically illustrates dual-slope voltage signals as a function of time simulated for a pickoff capacitor, such as pickoff capacitor $C_P$ shown in FIG. 6, having different values of capacitance. The voltage waveforms shown in FIG. 9 were produced through computer simulation using the following parameter values:

Pickoff Capacitor of Pressure Sensor $T_{R0}$=10 pF
Pickoff Capacitor of Pressure Sensor $TR_1$=11 pF
Pickoff Capacitor of Pressure Sensor $TR_2$=9 pF
Reference Capacitor=10 pF
$V_{ref}$=1 V
$V_{refdb2}$=544.5 mV
$I_{ch1}/I_{ch2}$=12
$I_{dch}/I_{ch2}$=12

It is noted that the expected gain associated with the simulated circuit was 2×, However, the realized gain was somewhat less (i.e., 1.8×), due to non-idealities such as stray capacitances, switch feed-through effects and the like.

It can be seen in FIG. 9 that the three voltage waveforms have different fast charge characteristics (e.g., from 0 V to knee in curve) and slow charge characteristics (from knee in curve to $V_{ref}$). As was discussed previously, the change in voltage of a capacitor may be expressed as:

$$\Delta V = I(\Delta t/C) \quad [43]$$

Since capacitance, C, forms part of the denominator, higher values of capacitance result in lower voltages at the dual-slope transition point (i.e., knee in the curve) of the voltage waveforms shown in FIG. 9, which effectively lowers the voltage switching level and thus the point at which the slow charging mode is initiated.

Equation [43] above may be rewritten as:

$$\Delta t = C(\Delta V/I) \quad [44]$$

From Equation [44] above, it can be seen that Δt increases as a function of increasing capacitance, C. Equations [43] and [44] further illustrates that ΔV is now dependent on pressure, thus providing for increased sensitivity to pressure changes. Since sensitivity is a function of Δt/T, increasing values of Δt provide for increased sensitivity.

With reference once again to FIG. 6 and to FIG. 1, a pressure sensor circuit 300, which incorporates pickoff capacitor, $C_P$, reference capacitor, $C_R$, and integrator circuit 301, suitable for processing pressure sensor signals in accordance with the principles of the present invention will now be described. The pressure sensor circuit 300 provided within pressure sensing module 20 translates the pressure modulated pickoff and reference capacitor values into charge time-modulated intervals, $T_{prs}$, between sensor current pulse signals, $P_R$ and $P_P$, transmitted up the active lead conductor 16.

The passive lead conductor 14 applies $V_{DD}$ from demodulator 150 to the $V_{DD}$ terminal of IC chip 64 and to the pickoff and reference capacitors, $C_P$ and $C_R$. The active lead conductor 16 connects the terminal VREG of IC chip 64 to the terminals CPOUT and CPIN of demodulator 150 through a resistor network.

The pressure sensor circuit 300 shown in FIG. 6 essentially operates as a bi-stable multivibrator operating near the target frequency of 5 kHz in alternately charging plate 86 of reference capacitor $C_R$ and plate of the pickoff capacitor $C_P$ from $V_{DD}$, which may be 0 volts, through a first (i.e., low) reference voltage, $V_{refdb2}$, and to a second (i.e., high) reference voltage, $V_{ref}$, through selective coupling to current sources 304 and 306. The reference capacitor, $C_R$, and the pickoff capacitor, $C_P$, are alternately discharged through a further current source 302 coupled to $V_{DD}$.

Additional details as to the operation of other portions of pressure sensor circuit 300 shown in FIG. 6 may be found in previously referenced U.S. Pat. Nos. 5,535,752 and 5,564,434 to Halperin. It will be readily appreciated by one skilled in the art that minor modifications to the operation of the circuitry disclosed in U.S. Pat. Nos. 5,535,752 and 5,564,434 may be made to accommodate the timing needs and switching between multiple current sources, such as current sources 302, 304, 306, and 308 shown in FIG. 6.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired. It will also be understood that the present invention may be implemented in dual-chamber pacemakers, cardioverters, defibrillators, or any implantable medical devices with similar sensors. Moreover, the multiple-slope integrator circuitry and techniques described above may be employed in other types of capacitive pickoff transducers, such as accelerometers and other motion sensors, or any capacitive pickoff based sensor component. For example, the above-described techniques and circuitry may be employed in the accelerometer of an activity sensor provided in an implantable medical device or in a capsule on a lead. For convient reference the sensors would be locatable in areas of implantable medical devices similar to those illustrated in FIG. 1 at 106 and 20. Such sensors would be advantageously sensitive to physiologic conditions other than pressure. Accordingly, all such variations and modifications are intended to be within the scope of the invention claimed by this letters patent.

What is claimed is:

1. A method of obtaining pressure data of a body fluid using a pressure sensor, the pressure sensor comprising a measurement capacitor responsive to changes in body fluid pressure, the method comprising:

charging, during a first charge period of an integration cycle, the measurement capacitor at a first charge rate;

charging, during a second charge period of the integration cycle, the measurement capacitor at a second charge rate; and producing, using the length of the first charge period and the second charge period of the measurement capacitor, a signal indicative of a pressure change of the body fluid imparted to the measurement capacitor.

2. The method of claim 1, wherein the signal is a signal indicative of a change in a time of integration.

3. The method of claim 1, wherein the signal is indicative of a time of integration having a sensitivity to the pressure change greater than a mechanical capacitive sensitivity of the measurement capacitor to the pressure change.

4. The method of claim 1, wherein a relative change in a time of integration, characterized by $\Delta t/T$, in response to the pressure change is greater than a relative change in a capacitance of the measurement capacitor, characterized by $\Delta C/C$, in response to the pressure change, where $\Delta t$ represents the change in integration time during the integration cycle of duration T, and $\Delta C$ represents the change in capacitance, C, of the measurement capacitor.

5. The method of claim 1, wherein the signal is a signal indicative of a change in capacitance of the measurement capacitor indicative of the body fluid pressure change.

6. The method of claim 1, wherein the signal is a voltage signal or a signal having a duty cycle indicative of the pressure change.

7. The method of claim 1, wherein:
charging the measurement capacitor at the first charge rate comprises charging the measurement capacitor using a first current source; and
charging the measurement capacitor at the second charge rate comprises charging the measurement capacitor using a second current source.

8. The method of claim 7, further comprising switching connectivity of the measurement capacitor from the first current source to the second current source in response to a switch signal.

9. The method of claim 8, wherein the switch signal is produced by a timing circuit.

10. The method of claim 8, wherein the pressure sensor further comprises a reference capacitor substantially insensitive to conditions of pressure, further wherein the switch signal is produced by the reference capacitor or a timing circuit.

11. The method of claim 1, wherein the first charge rate is greater than the second charge rate.

12. The method of claim 1, further comprising varying a duration of the first charge period or a duration of the second charge period.

13. A circuit for detecting a pressure change of a body fluid, comprising:
a pressure sensor comprising a measurement capacitor responsive to pressure changes of the body fluid;
a switch coupled to the measurement capacitor;
a first current source coupled to the switch;
a second current source coupled to the switch; and
a timing circuit, the switch coupling the first current source to the measurement capacitor for charging the measurement capacitor at a first charge rate during a first charge period of an integration cycle, and the switch, in response to a switch signal produce by the timing circuit, coupling the second current source to the measurement capacitor for charging the measurement capacitor at a second charge rate during a second charge period of the integration cycle, the pressure sensor producing a signal indicative of a pressure change of the body fluid imparted to the measurement capacitor.

14. The circuit of claim 13, wherein the signal produced by the pressure sensor is a signal indicative of a change in a time of integration.

15. The circuit of claim 13, wherein the signal produced by the pressure sensor is indicative of a time of integration having a sensitivity to the pressure change greater than a mechanical capacitive sensitivity of the measurement capacitor to the pressure change.

16. The circuit of claim 13, wherein a relative change in a time of integration, characterized by $\Delta t/T$, in response to the pressure change is greater than a relative change in a capacitance of the measurement capacitor, characterized by $\Delta C/C$, in response to the pressure change, where $\Delta t$ represents the change in integration time during the integration cycle of duration T, and $\Delta C$ represents the change in capacitance, C, of the measurement capacitor.

17. The circuit of claim 13, wherein the signal produced by the pressure sensor is a signal indicative of a change in capacitance of the measurement capacitor indicative of the body fluid pressure change.

18. The circuit of claim 13, wherein the signal produced by the pressure sensor is a voltage signal or a signal having a duty cycle indicative of the pressure change.

19. The circuit of claim 13, wherein the timing circuit comprises a reference capacitor substantially insensitive to conditions of pressure, and the switch signal is produced by the reference capacitor.

20. The circuit of claim 13, wherein the first charge rate is greater than the second charge rate.

21. The circuit of claim 13, wherein the timing circuit varies a duration of the first charge period or a duration of the second charge period.

22. A body implantable pressure sensing apparatus, comprising:
an implantable medical device;
a lead coupled to the implantable medical device; and
a pressure sensor provided on the lead, the pressure sensor, comprising:
a measurement capacitor responsive to pressure changes of a body fluid;
a switch coupled to the measurement capacitor;
a first current source coupled to the switch;
a second current source coupled to the switch; and
a timing circuit, the switch coupling the first current source to the measurement capacitor for charging the measurement capacitor at a first charge rate during a first charge period of an integration cycle, and the switch, in response to a switch signal produce by the timing circuit, coupling the second current source to the measurement capacitor for charging the measurement capacitor at a second charge rate during a second charge period of the integration cycle, the pressure sensor producing a signal indicative of a pressure change of the body fluid imparted to the measurement capacitor.

23. The apparatus of claim 22, wherein the implantable medical device comprises a pacemaker, a pacemaker/cardioverter/defibrillator (PCD) or a hemodynamic monitor.

24. The apparatus of claim 22, wherein the signal produced by the pressure sensor is indicative of a time of integration having a sensitivity to the pressure change greater than a mechanical capacitive sensitivity of the measurement capacitor to the pressure change.

25. The apparatus of claim 22, wherein a relative change in a time of integration, characterized by $\Delta t/T$, in response to the pressure change is greater than a relative change in a capacitance of the measurement capacitor, characterized by $\Delta C/C$, in response to the pressure change, where $\Delta t$ represents the change in integration time during the integration cycle of duration T, and $\Delta C$ represents the change in capacitance, C, of the measurement capacitor.

26. The apparatus of claim 22, wherein the signal produced by the pressure sensor is a signal indicative of a change in capacitance of the measurement capacitor indicative of the body fluid pressure change.

27. The apparatus of claim 22, wherein the signal produced by the pressure sensor is a voltage signal or a signal having a duty cycle indicative of the pressure change.

28. The apparatus of claim 22, wherein the timing circuit comprises a reference capacitor substantially insensitive to conditions of pressure, and the switch signal is produced by the reference capacitor.

29. The apparatus of claim 22, wherein the first charge rate is greater than the second charge rate.

30. The apparatus of claim 22, wherein the timing circuit varies a duration of the first charge period or a duration of the second charge period.

31. A method of obtaining physiologic data of a body tissue using a capacitive pickoff sensor, the capacitive pick-off sensor comprising a measurement capacitor responsive to conditions of a physiologic condition, the method comprising:

charging, during a first charge period of an integration cycle, the measurement capacitor at a first charge rate;

charging, during a second charge period of the integration cycle, the measurement capacitor at a second charge rate; and producing, using the lengths of the first and second charge periods of the measurement capacitor, a signal indicative of physiologic condition of the body fluid imparted to the measurement capacitor.

32. The method of claim 31, wherein the signal is a signal indicative of a change in a time of integration.

33. The method of claim 31, wherein the signal is indicative of a time of integration having a sensitivity to the physiologic condition greater than a mechanical capacitive sensitivity of the measurement capacitor to the physiologic condition.

34. A body implantable physiologic condition sensing apparatus, comprising:

an implantable medical device;

a sensor housing coupled to the implantable medical device; and a capacitive pickoff sensor provided in the or housing, the sensor, comprising:

a measurement capacitor responsive to physiologic condition of a body tissue;

a switch coupled to the measurement capacitor;

a first current source coupled to the switch;

a second current source coupled to the switch; and a timing circuit, the switch coupling the first current source to the measurement capacitor for charging the measurement capacitor at a first charge rate during a first charge period of an integration cycle, and the switch, in response to a switch signal produce by the timing circuit, coupling the second current source to the measurement capacitor for charging the measurement capacitor at a second charge rate during a second charge period of the integration cycle, the physiologic condition sensor producing a signal indicative of a physiologic condition of the body tissue imparted to the measurement capacitor.

* * * * *